United States Patent [19]

Wollweber et al.

[11] Patent Number: 4,977,182

[45] Date of Patent: Dec. 11, 1990

[54] FUNGICIDAL 3-CYANO-4-PHENYL-PYRROLES

[75] Inventors: Detlef Wollweber, Wuppertal; Wilhelm Brandes, Leichlingen; Stefan Dutzmann, Duesseldorf, all of Fed. Rep. of Germany

[73] Assignee: Bayer Aktiengesellschaft, Leverkusen, Fed. Rep. of Germany

[21] Appl. No.: 336,983

[22] Filed: Apr. 12, 1989

[30] Foreign Application Priority Data

Apr. 29, 1988 [DE]  Fed. Rep. of Germany ....... 3814478

[51] Int. Cl.$^5$ ..................... A01N 43/36; C07D 207/34
[52] U.S. Cl. .................... 514/423; 548/531; 548/540
[58] Field of Search ................ 548/531, 540; 514/423

[56] References Cited

U.S. PATENT DOCUMENTS 4,229,465  10/1980  Ohkuma et al. .................... 548/540

FOREIGN PATENT DOCUMENTS 0236272  9/1987  European Pat. Off. .
2927480  1/1980  Fed. Rep. of Germany .

Primary Examiner—Joseph Paul Brust
Assistant Examiner—Mary Sue Howard
Attorney, Agent, or Firm—Sprung Horn Kramer & Woods

[57]     ABSTRACT

Fungicidal 3-cyano-4-phenyl-pyrroles of the formula

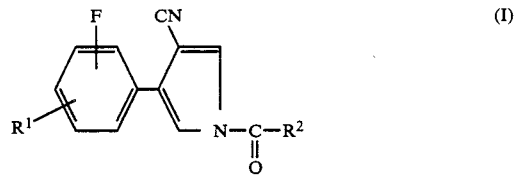

in which
R$^1$ stands for halogen, alkyl, alkoxy, alkylthio, halogenoalkyl, halogenoalkoxy or halogenoalkylthio and
R$^2$ stands for alkyl, alkoxy or alkoxyalkyl.

9 Claims, No Drawings

FUNGICIDAL 3-CYANO-4-PHENYL-PYRROLES

The invention relates to new 3-cyano-4-phenylpyrroles, a process for their preparation and their use in pesticides.

It has been disclosed that certain 3-cyano-4-phenylpyrroles, such as, for example, the compound 3-cyano-4-(2,3-dichlorophenyl)-pyrrole or the compound 1-acetyl-3-cyano-4-(2,3-dichlorophenyl)-pyrrole, possess fungicidal activity (cf., for example, EP 236,272; DE-OS (German Published Specification) 2,927,480).

However, the activity of these previously known compounds is not completely satisfactory in all fields of application, in particular at low application rates and concentrations.

New 3-cyano-4-phenyl-pyrroles of the general formula (I)

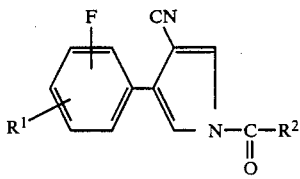   (I)

in which
R$^1$ stands for halogen, alkyl, alkoxy, alkylthio halogenoalkyl, halogenoalkoxy or halogenoalkylthio and
R$^2$ stands for alkyl, alkoxy or alkoxyalkyl, have been found.

Furthermore, it has been found that the new 3-cyano-4-phenyl-pyrroles of the general formula (I)

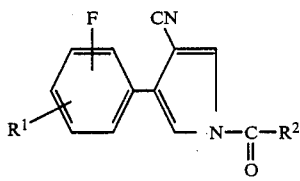   (I)

in which
R$^1$ stands for halogen, alkyl, alkoxy, alkylthio, halogenoalkyl, halogenoalkoxy or halogenoalkylthio and
R$^2$ stands for alkyl, alkoxy or alkoxyalkyl, are obtained when 1H-3-cyano-4-phenyl-pyrroles of the formula (II)

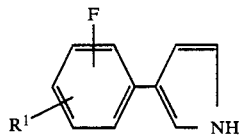   (II)

in which
R$^1$ has the abovementioned meaning, are reacted with acylating agents of the formula (III)

   (III)

in which
R$^2$ has the abovementioned meaning and
E stand for an electron-withdrawing leaving group, if appropriate in the presence of a diluent and if appropriate in the presence of a reaction auxiliary.

Finally, it has been found that the new 3-cyano-4-phenyl-pyrroles of the general formula (I) possess a good action against pests.

Surprisingly, the 3-cyano-4-phenyl-pyrroles of the general formula (I), inter alia, show a considerably better fungicidal activity than the 3-cyano-4-phenyl-pyrroles which are known from the prior art, such as, for example, 3-cyano-4-(2,3-dichlorophenyl)-pyrrole, which are chemically similar compounds of a similar type of action.

Formula (I) provides a general definition of the 3-cyano-4-phenyl-pyrroles according to the invention. Preferred compounds of the formula (I) are those in which
R$^1$ stands for fluorine, chlorine, bromine, iodine, for in each case straight-chain or branched alkyl, alkoxy or alkylthio, each having 1 to 4 carbon atoms, or for in each case straight-chain or branched halogenoalkyl, halogenoalkoxy or halogenoalkylthio, each having 1 to 4 carbon atoms and 1 to 9 identical or different halogen atoms, and
R$^2$ stands for in each case straight-chain or branched alkyl, alkoxy or alkoxyalkyl, each having 1 to 6 carbon atoms in the individual alkyl moieties.

Particularly preferred compounds of the formula (I) are those in which
R$^1$ stands for fluorine, chlorine, bromine, methyl, ethyl, methoxy, ethoxy, methylthio, trifluoromethyl, trifluoromethoxy or trifluoromethylthio and
R$^2$ stands for in each case straight-chain or branched alkyl, alkoxy or alkoxyalkyl, each having 1 to 4 carbon atoms in the individual alkyl moieties.

Very particularly preferred compounds of the formula (I) are those in which
R$^1$ stands for fluorine, chlorine, methyl, trifluoromethyl or trifluoromethoxy and
R$^2$ stands for methyl, ethyl, methoxy, ethoxy, methoxymethyl or ethoxymethyl.

In addition to the compounds mentioned in the Preparation Examples, the following 3-cyano-4-phenyl-pyrroles of the general formula (I) may be mentioned individually:

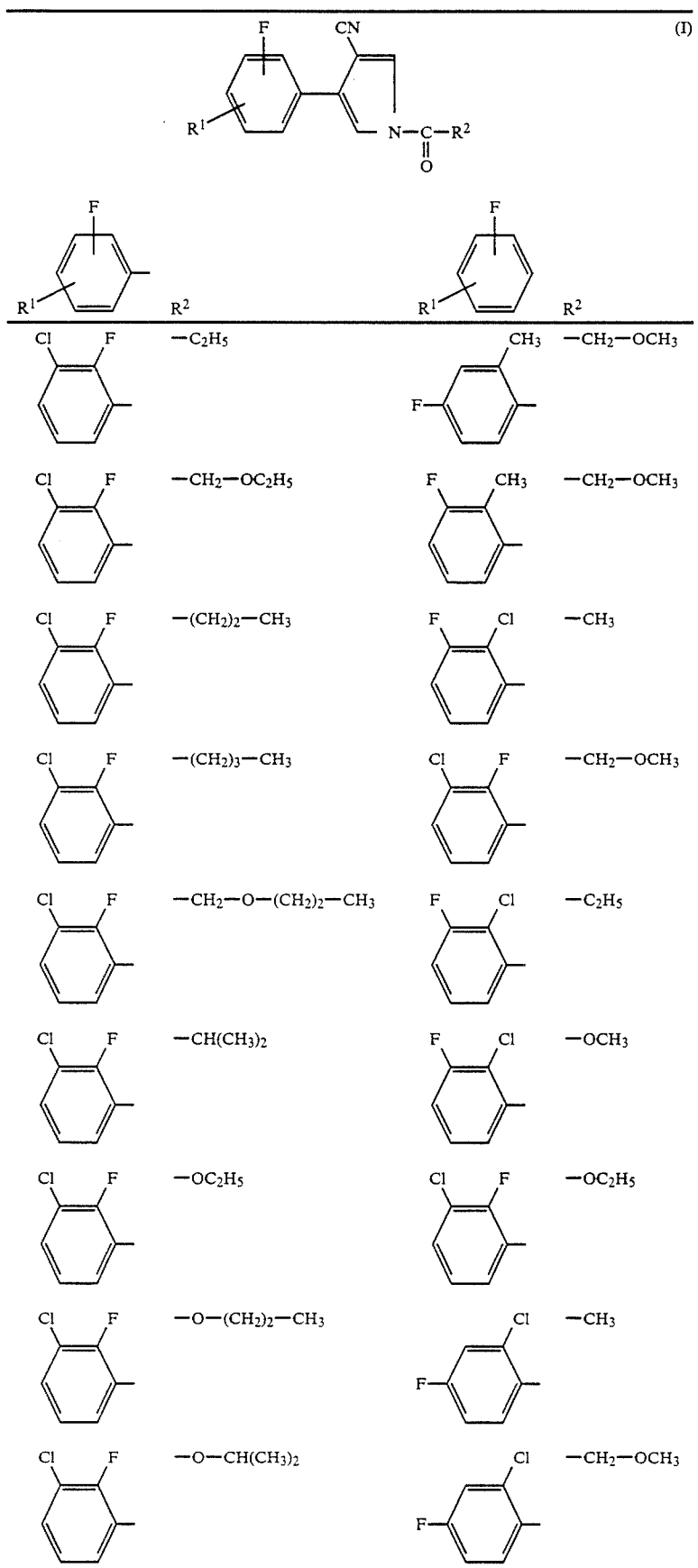

-continued
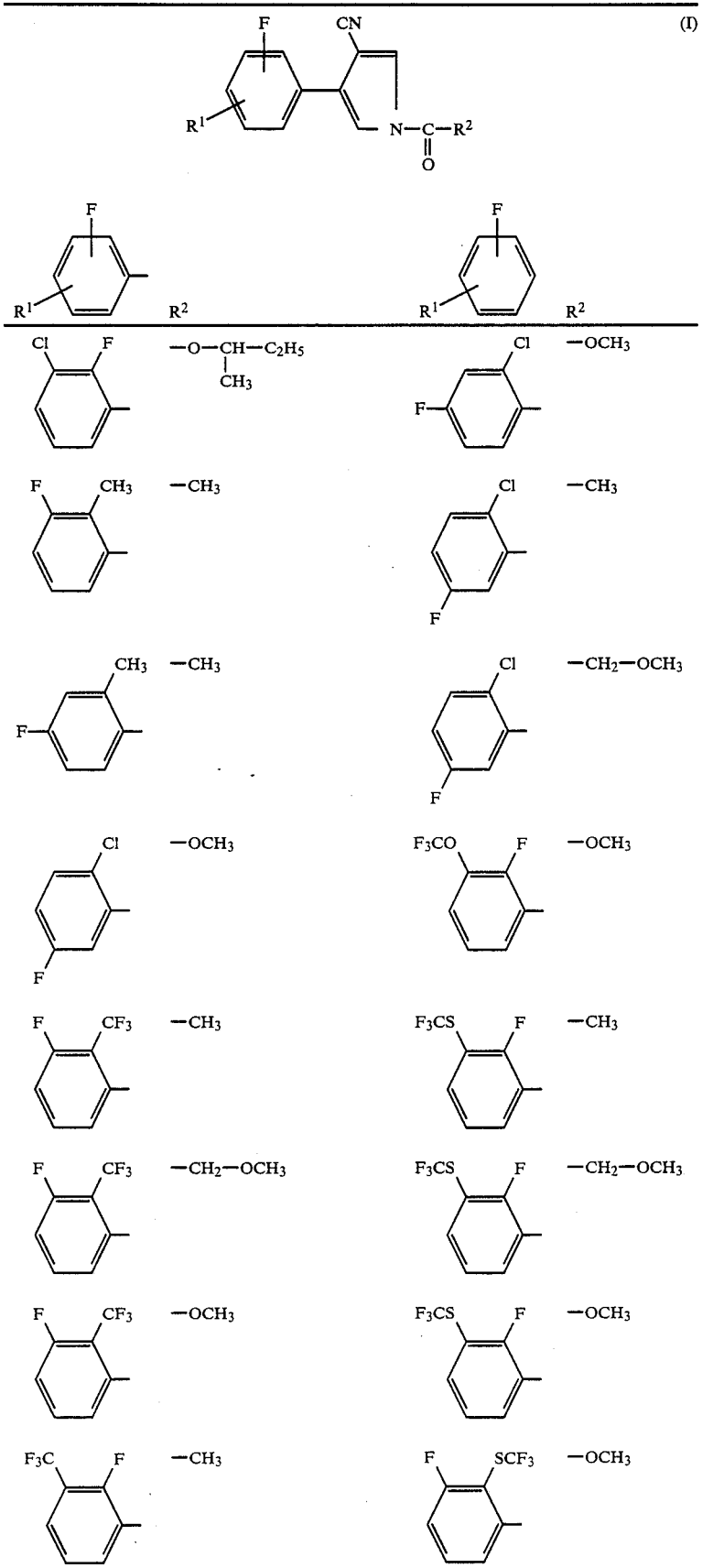

-continued
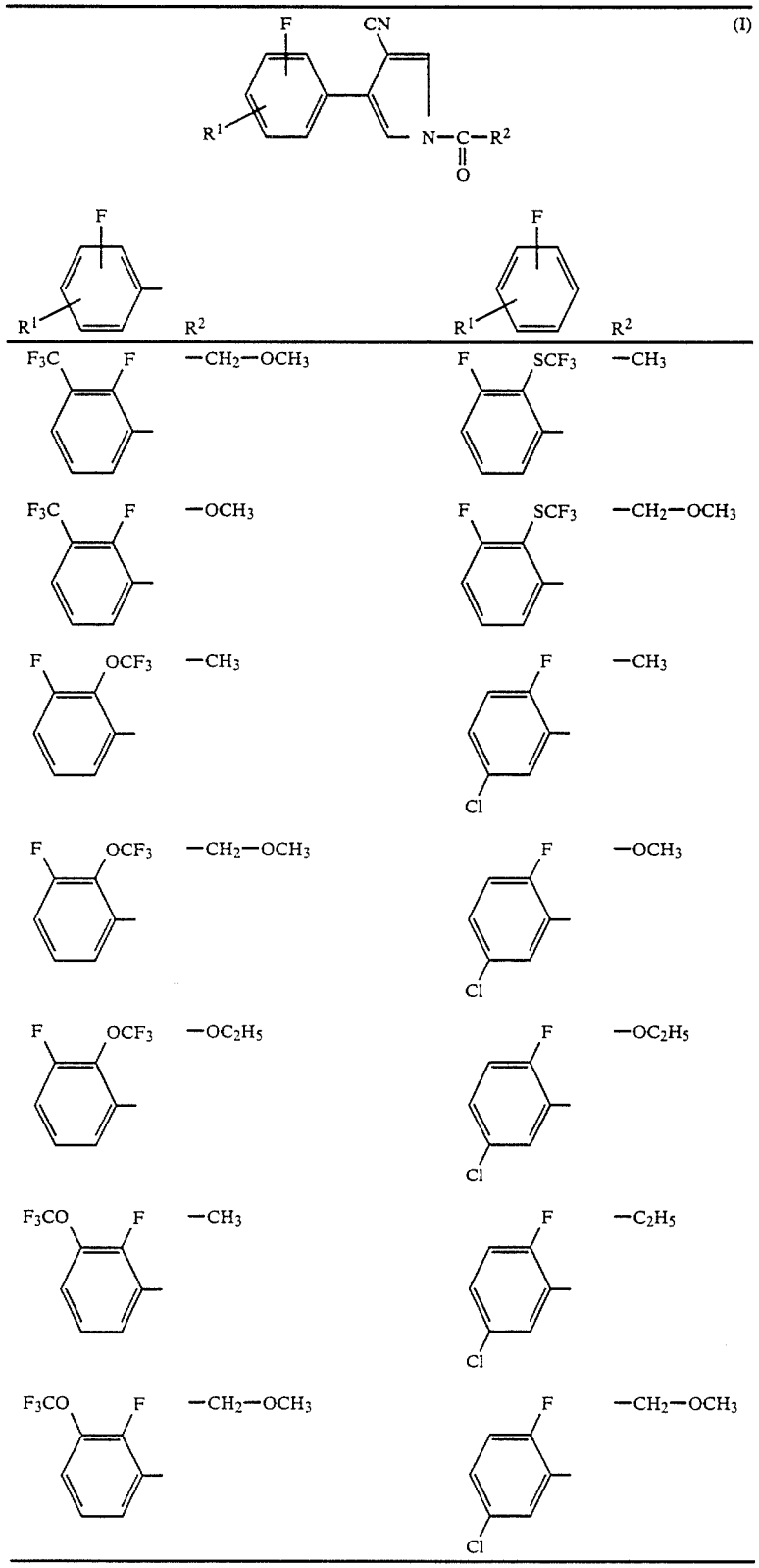
If, for example, 3-cyano-4-(2-fluoro-3-chlorophenyl)-pyrrole and ethyl chloroformate are used as starting substances, the course of the reaction of the process according to the invention may be represented by the following equation:

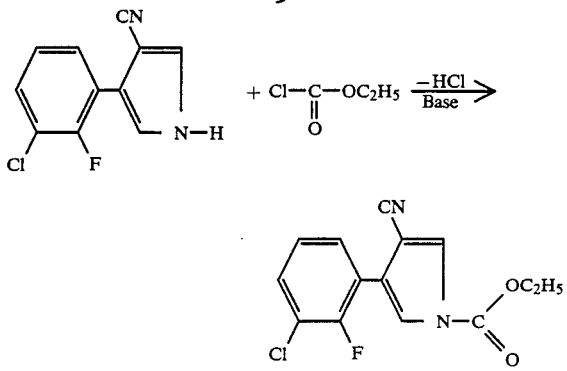

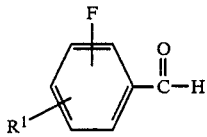

Formula (II) provides a general definition of the 1H-3-cyano-4-phenyl-pyrroles required as starting substances for carrying out the process according to the invention. In this formula (II), Ar preferably stands for those radicals which have already been mentioned in connection with the description of the substances of the formula (I) according to the invention as being preferred for this substituent.

The 1H-3-cyano-4-phenyl-pyrroles of the formula (II) are the subject matter of Application Ser. No. 266,966, filed Nov. 3, 1988, corresponding to German Patent Application P 3,737,984, of Nov. 9, 1987, and they can be obtained in analogy to known processes (cf., for example, EP 236,272, DE-OS (German Published Specification) 2,927,480), for example by a process in which (a) fluoroanilines of the formula (IV)

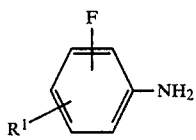 (IV)

in which

R¹ has the abovementioned meaning, are initially reacted in a first step with acrylonitrile under customary diazotization conditions, for example in the presence of sodium nitrite and hydrochloric acid, and in the presence of a suitable metal salt catalyst, such as, for example, copper(II) chloride or copper(II) oxide, and if appropriate in the presence of a suitable diluent, such as, for example, acetone or water, at temperatures between −20° C. and +50° C. ("Meerwein arylation"; cf. in this context also Organic Reactions 11, 189 [1960]; Organic Reactions 24, 225 [1976] or C. Ferri "Reaktionen der organischen Synthese" [Reactions in Organic Synthesis] p.319, Thieme Verlag Stuttgart 1978), and then in a second step the resulting substituted α-chloro-β-phenylpropionitriles of the formula (V)

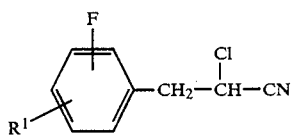 (V)

in which

R¹ has the abovementioned meaning, are dehydrohalogenated with bases, such as, for example, triethylamine or diazabicycloundecene, in a customary manner and if appropriate in the presence of a diluent, such as, for example, tetrahydrofuran, at temperatures between 0° C. and 50° C. (cf. also the Preparation Examples) or, alternatively, by a process in which (b) substituted benzaldehydes of the formula (VI)

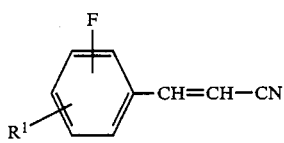 (VI)

in which

R¹ has the abovementioned meaning,
are condensed with cyanoacetic acid of the formula (VII)

$$NC-CH_2-COOH \quad (VII)$$

in a customary manner in the presence of a base, such as, for example, piperidine or pyridine, and if appropriate in the presence of a suitable diluent, such as, for example, pyridine, at temperatures between 50° C. and 120° C. and simultaneously decarboxylated (cf., for example, "Organikum [Laboratory Practical of Organic Chemistry]" p. 571/572; 15th edition; VEB Deutscher Verlag der Wissenschaften Berlin 1981, and also the Preparation Examples), and the resulting substituted cinnamonitriles obtained by process (a) or (b)] of the formula (VIII)

 (VIII)

in which

R¹ has the abovementioned meaning, are reacted with sulphonylmethyl isocyanides of the formula (IX)

$$R^3-SO_2-CH_2-NC \quad (IX)$$

in which

R³ stands for alkyl or for optionally substituted aryl, in particular for methyl, for 4-methylphenyl, 4-chlorophenyl or for phenyl, in the presence of a base, such as, for example, sodium hydride, and if appropriate in the presence of a diluent, such as, for example, tetrahydrofuran, at temperatures between −20° C. and +50° C.

Some of the fluoroanilines of the formula (IV) are known (cf, for example, J. org. Chem. 39, 1758–1761 [1974]; J. med. Chem. 12, 195–196 [1969] or US-PS 3,900,519).

Fluoroanilines of the formula (IVa)

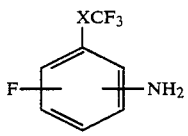 (IVa)

in which

X stands for oxygen or sulphur, are the subject matter of Application Ser. No. 266,966, filed Nov. 3, 1988, now pending, corresponding to German Patent Application P 3,737,985 of Nov. 9, 1987.

A generally applicable process for the preparation of compounds of the formula (IVa)

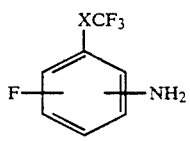
(IVa)

in which
X stands for oxygen or sulphur,
is characterized in that compounds of the formula (X)

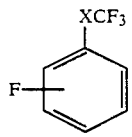
(X)

in which
X has the abovementioned meaning,
are nitrated and the resulting nitro compounds are reduced.

The fluorine-containing trifluoromethoxy- and trifluoromethylthiobenzenes of the formula (X), which are to be employed in this process, are known (cf., for example, J. org. chem. 29, 1 [1964]).

The nitration can be carried out using customary nitrating agents, for example, using mixtures of nitric acid and sulphuric acid. In this process, the temperature can be in the range 0 to 80° C., preferably it is between 20 and 50° C. The nitrating agents can be employed for example in such amounts that 0.8 to 1.5 moles of nitrating agent are formed in the reaction mixture per mole of starting compound. Preferably, 1 to 1.1 moles of nitrating agent are allowed to form per mole of starting compound. If required, the nitration can be carried out in the presence of an inert organic solvent. Methylene chloride is a suitable example.

The subsequent reduction can be carried out chemically, i.e., for example using metals having a reducing action or metal salts. Iron, zinc, tin, tin(II) chloride or titanium(III) chloride are suitable examples. Reducing agents of this type are preferably employed in the stoichiometrically required amount. For a reduction of this type, the nitro compounds can be employed for example in the form in which they are obtained in the nitration, or they can be isolated subsequently. The reduction can also be carried out catalytically using hydrogen, it being possible, for example, to employ catalysts containing metals or consisting thereof. Suitable metals are for example those of sub-group VIII of the Periodic Table of the Elements, in particular palladium, platinum and nickel. The metals can be present in elementary form or in the form of compounds, and also in particularly activated forms, for example, in the form of Raney metals or applied as metals or metal compounds fixed to support materials. Raney nickel or paLLadium on charcoal or aluminum oxide is preferred.

The catalytic reduction is preferably carried out in the presence of a solvent. Examples of suitable solvents are alcohols or ethers, such as methanol, ethanol or tetrahydrofuran. The catalytic reduction can be carried out, for example, at temperatures in the range 0 to 80° C. and, for example, at hydrogen pressures in the range 1 to 100 bar. Excess hydrogen is generally not critical.

Preferably, acid-free nitro compounds are employed for the catalytic reduction. Thus, if necessary, the former are to be freed from acids, for example by washing with water or neutralization with bases, such as, for example, sodium hydrogen carbonate.

Working up of the reaction mixture present after the chemical reduction or the catalytic hydrogenation can be carried out, for example, in such a way that initially any solid constituents present are filtered off and the filtrate is distilled, if necessary after washing with water. If an isomer mixture is obtained as the reaction product, it can be resolved by precision distillation.

Compounds of the formula (IVa) where fluorine is in the o- and p-position relative to the amino group can also be prepared by reacting compounds of the formula (XI)

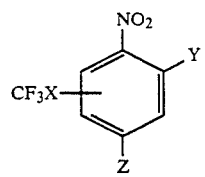
(XI)

in which
X stands for oxygen or sulphur and either
Y or Z stands for chlorine, the radical which does not stand for chlorine in each case standing for hydrogen,
with potassium fluoride in the presence of tetramethylene sulphone, any chlorine present being replace by fluorine and then carrying out a reduction, in which process the nitro group is converted to an amino group.

Compounds of the formula (XI) are known (cf. Houben-Weyl, Methoden der organischen Chemie [Methods of Organic Chemistry] E 4, p. 633 et seq; Chem. Ber. 96, 48-55 [1963]).

For example, 0.5 to 3 moles of potassium fluoride can be employed per mole of compound of the formula (XI). Preferably, this amount is 1.2 to 1.5 moles. Tetramethylene sulphone acts as the solvent and is preferably employed in at least such an amount that a reaction mixture is present which can readily be stirred. Relatively large amounts of solvent do not interfere with the reaction.

Suitable temperatures for the reaction with potassium fluoride in tetramethylene sulphone are for example those in the range 160 to 230° C. Preferred temperatures are those from 180 to 210° C. Preferably, the reaction is carried out in an environment which is as free of water as possible. This can be achieved for example by employing the compound of the formula (XI) in carefully dried form as the last component and distilling off a small amount of tetramethylene sulphone together with any water present from the other components which have previously been combined.

When the reaction is complete, solids present in the reaction mixture and if desired all or part of the tetramethylene sulphone can be removed.

The subsequent reduction of the nitro group to the amino group and working up of the reaction mixture which is then present can be carried out as has been described above in the generally applicable process for the preparation of compounds of the formula (IVa).

Alternatively, compounds of the formula (IVa) in which X stands for oxygen can also be prepared by reacting compounds of the formula (XII)

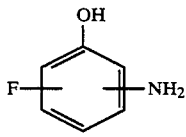

with carbon tetrachloride in the presence of hydrogen fluoride, in which process the OH group is converted to an F₃CO group.

Compounds of the formula (XII) have been disclosed (cf. FR Pat. 2,446,805).

For example, 1 to 10 moles of carbon tetrachloride and 5 to 30 moles of hydrogen fluoride can be employed per mole of the particular compound of the formula (XII). Even relatively large excesses of carbon tetrachloride and hydrogen fluoride generally do not interfere with the reaction. Suitable reaction temperatures are for example those in the range 100 to 150° C. This process is preferably carried out under pressure, for example by releasing the hydrogen chloride gas which is formed only above a certain pressure. This pressure can for example be between 18 and 60 bar. If necessary, an inert gas can additionally be injected, for example 1 to 20 bar nitrogen. It is advantageous to stir well during the reaction.

Working up of the reaction mixture can be carried out for example in such a way that the reaction mixture is cooled to room temperature and released, and excess hydrogen fluoride and excess carbon tetrachloride is distilled off for example at temperatures up to 80° C., the residue is transferred into ice water, the mixture is rendered alkaline using sodium hydroxide solution and the organic phase is extracted using dichloromethane and subjected to a precision distillation after drying.

Other new compounds of the formula (IVb)

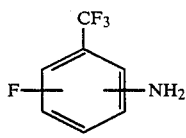

and those in which the trifluoromethyl 1-position and
(a) the amino group is in the 2-position and the fluorine atom in the 6-position or
(b) the amino group is in the 3-position and the fluorine atom in the 2-position.

They are the subject matter of Application Ser. No. 266,966, filed Nov. 3, 1988, now pending, corresponding to German Patent Application P 3,737,986 of Nov. 9, 1987.

A preferred process for the preparation of fluorine-containing trifluoromethylaminobenzenes in which the trifluoromethyl group is in the 1-position and
(a) the amino group is in the 2-position and the fluorine atom in the 6-position or
(b) the amino group is in the 3-position and the fluorine atom in the 2-position;
is characterized in that corresponding fluorine-containing trifluoromethylbenzenes are nitrated and the resulting fluorine-containing trifluoromethylnitrobenzenes are reduced.

The fluorine-containing trifluoromethylbenzenes, which are, however, free of amino groups, to be employed in this process according to the invention are known (cf., for example, J. chem. Soc. C, 1971, 1547–1549). The nitration, the subsequent reduction and working up of the compounds of the formula (IVb) are carried out under the conditions described for the preparation of compounds of the formula (IVa).

Another process specifically for the preparation of fluorine-containing trifluoromethylaminobenzenes in which the trifluoromethyl group is in the 1-position and
(a') the amino group is in the 2-position and one fluorine atom in the 6-position or
(b') the amino group is in the 4-position and one fluorine atom in the 2-position,
is characterized in that corresponding fluorine-containing 2- and/or 4-halogeno-trifluoromethylbenzenes are reacted with ammonia in the presence of an organic solvent and under increased pressure.

The 2- and/or 4-halogeno-trifluoromethylbenzenes to be employed in this process have been disclosed (cf., for example, EP 34,402).

The ammonia can be added in liquid or gaseous form, for example as a substance (gaseous or liquid) or as an aqueous solution. For example, 1 to 10 moles of ammonia can be used per mole of halogen atoms to be replaced in the 2- and/or 4-position by NH₂ groups. This amount is preferentially 3 to 8 moles. Suitable temperatures for this reaction are for example those in the range 80 to 160° C., those in the range 100 to 130° C. are preferred. The reaction can be carried out under the inherent pressure, of the ammonia, which arises in the sealed vessel at reaction temperature, which pressure can be for example in the range 10 to 20 bar. Higher pressures can also be applied, for example those up to 100 bar.

Solvents which can be employed for this reaction are inert or substantially inert organic solvents of a variety of types. Suitable examples are alcohols, ethers, sulphones or aromatic hydrocarbons.

The desired reaction product(s) can be obtained from the reaction mixture which is present after the reaction for example by initially cooling the reaction mixture and releasing the pressure, then removing the solvent and subsequently carrying out a distillation, preferably under reduced pressure.

Most of the fluorobenzaldehydes of the formula (VI) also required as precursors for the preparation of the new starting materials of the formula (II) according to variant b) are known (cf., for example, Chem. Abstr. 100: 209 388k or Jap. Pat. 58/222 045), for example, 5-fluoro2-trifluoromethyl benzaldehyde is registered under the Reg. No. 90 381-08-1, 3-chloro-5-fluoro-benzaldehyde under Reg. No. 90 390-49-1 and 3-chloro-6-fluoro-benzaldehyde under Reg. No. 96 515-79-6 in Chem. Abs. Cyanoacetic acid, of the formula (VII), is a generally known compound of organic chemistry.

The sulphonylmethyl isocyanides of the formula (IX) also required as precursors for the preparation of the new starting materials of the formula (II) are likewise known (cf., for example, Synthesis 1985, 400–402; Org. Syntheses 57, 102–106 [1977]; J. org. Chem. 42, 1153–1159 [1977]; Tetrahedron Lett. 1972, 2367–2368).

Formula (III) provides a general definition of the acylating agent also required as starting substances for carrying out the process according to the invention. In this formula (III), R preferably stands for those radicals which have already been mentioned in connection with the description of the substances of the formula (I) according to the invention as being preferred for this substituent.

E preferably stands for halogen, in particular for chlorine or bromine, or for an anhydride radical of the formula

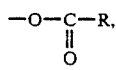

where R has the abovementioned meaning.

The acylating agents of the formula (III) are generally known compounds of organic chemistry.

As an alternative to the preparation of the precursors of the formula (II) with the aid of the previously described preparation processes, a variety of other preparation processes for the preparation of the precursors of the formula (II) may be considered.

For example, 1H-3-cyano-4-phenyl-pyrroles of the formula (II) are also obtained when α-cyanocinnamic acid esters are reacted with p-toluene-sulphonylmethyl isocyanide in the presence of bases and in the presence of copper(II) salts (cf. J6-1030-571 or J6-1200-984) or when α-substituted cinnamonitriles are cyclized with isocyanoacetic acid esters in the presence of sodium hydride, the resulting pyrrole-2-carboxylic acid esters are hydrolyzed with bases and then thermally decarboxylated (cf. JP 59/212 468) or when phenacylamine derivatives are reacted with suitably substituted acrylonitrile derivatives (cf. EP 174,910) or when 3-trifluoromethyl-4-phenyl-pyroles are reacted with ammonia at increased temperature and increased pressure (cf. EP 182,738) or when 3-cyano-4-phenyl-$\Delta^2$-pyrrolines are oxidized in the presence of copper(II) salts or iron-(III) salts (cf. EP 183,217) or when α-cyanoacrylic acid derivatives are reacted with isocyanoacetic acid esters in the presence of a base and the resulting $\Delta^2$-pyrroline-2-carboxylic acid derivatives are oxidatively decarboxylated in a second step in the presence of a base and in the presence of a metal salt catalyst cf. German Patent Application P 3,718,375 dated 02.06.1987).

Suitable diluents for carrying out the process according to the invention are inert organic solvents. These include in particular aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

The process according to the invention is preferably carried out in the presence of a suitable reaction auxiliary. Suitable reaction auxiliaries are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

When carrying out the process according to the invention, the reaction temperatures can be varied within a relatively wide range. In general, the process is carried out at temperatures between −20° C. and 150° C., preferably at temperatures between 0° C. and 80° C.

For carrying out the process according to the invention, 1.0 to 5.0 moles, preferably 1.0 to 1.5 moles, of acylating agents of the formula (III) and if appropriate 1.0 to 5.0 moles, preferably 1.0 to 1.5 moles, of reaction auxiliary are employed per mole of 1H-3-cyano-4-phenyl-pyrrole of the formula (II).

The reaction is carried out, and the reaction products are worked up and isolated by generally customary methods (cf. also the Preparation Examples).

The active compounds according to the invention exhibit a powerful action against pests and can be employed in practice for combating undesired noxious organisms. The active compounds are suitable, for example, for the use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, Pythium ultimum; Phytophthora species, such as, for example, Phytophthora infestans; Pseudoperonospora species, such as, for example, Pseudoperonospora humuli or Pseudoperonospora cubensis; Plasmopara species, such as, for example, Plasmopara viticola; Peronospora species, such as, for example, Peronospora pisi or P. brassicae; Erysiphe species, such as, for example, Erysiphe graminis; Sphaerotheca species, such as, for example, Sphaerotheca fuliginea; Podosphaera species, such as, for example, Podosphaera leucotricha; Venturia species, such as, for example, Venturia inaequalis; Pyrenophora species, such as, for example, Pyrenophora teres or P. graminea (conidia form: Drechslera, syn: Helminthosporium); Cochliobolus species, such as, for example, Cochliobolus sativus (conidia form: Drechslera, syn: Helminthosporium); Uromyces species, such as, for example, Uromyces appendiculatus; Puccinia species, such as, for example, Puccinia recondita; Tilletia species, such as, for example, Tilletia caries; Ustilago species, such as, for example, Ustilago nuda or Ustilago avenae; Pellicularia species, such as, for example, Pellicularia sasakii; Pyricularia species, such as, for example, Pyricularia oryzae; Fusarium species, such as, for example, Fusarium culmorum; Botrytis species, such as, for example, Botrytis cinerea; Septoria species, such as, for example, Septoria nodorum; Leptosphaeria species, such as, for example, Leptosphaeria nodorum; Cercospora species, such as, for example, Cercospora canescens; Alternaria species, such as, for example, Alternaria brassicae and Pseudocercosporella species, such as, for example, Pseudocercosporella herpotrichoides.

The good toleration, by plants, of the active compounds in the concentrations required for combating plant diseases permits a treatment of above-ground parts of plants, of vegetative propagation stock and seeds, and of the soil.

Here, the active compounds according to the invention can be employed with particularly good success for combating diseases in fruit growing and vegetable growing, such as, for example, against the causative organism of gray mold of beans (Botrytis cinerea) or for combating rice diseases, such as, for example, against the causative organism of rice blast disease (Pyricularia oryzae) or for combating cereal diseases, such as, for example, against the causative organism of glume blotch of wheat (Leptosphaeria nodorum) or against the causative organism of cereal snow mold (Fusarium nivale). Moreover, the active compounds according to the invention possess a good fungicidal activity when applied in vitro.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

Preparation Examples

EXAMPLE 1

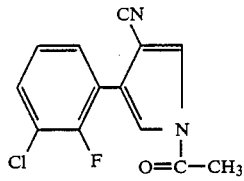

1.46 g (0.0143 mole) of acetic anhydride, 1.45 g (0.0143 mole) of triethylamine and 0.2 g of 4-dimethylaminopyridine are added to 3.0 g (0.136 mole) Df 3-cyano-4-(2-fluoro-3-chlorophenyl)-pyrrole in a mixture of 120 ml of dichloromethane/tetrahydrofuran (5:1), and the mixture is stirred for 16 hours at room temperature, washed twice with water, dried over sodium sulphate and concentrated in vacuo.

2.4 g (67.2% of theory) of 1-acetyl-3-cyano-4-(2-fluoro-3-chlorophenyl)-pyrrole of melting point 141° C.–142° C. are obtained.

EXAMPLE 2

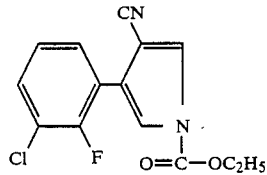

4.0 g (0.0182 mole) of 3-cyano-4-(2-fluoro-3-chlorophenyl)-pyrrole in 60 ml of dimethoxyethane are added dropwise, with stirring and at room temperature to 0.65 g (0.022 mole) of sodium hydride (80 per cent strength in paraffin oil) in 20 ml of dimethoxyethane, and the mixture is then stirred for two more hours at room temperature. After this, 3.4 g (0.032 mole) of ethyl chloroformate, dissolved in 20 ml of dimethoxyethane, are added dropwise, with stirring and likewise at room temperature, the mixture is stirred for 3 more hours at room temperature, hydrolysed with water, extracted using ethyl acetate, washed twice with water and dried over sodium sulphate, and the solvent is removed in vacuo.

4.9 g (92% of theory) of 1-ethoxycarbonyl-3-cyano-4-(2-fluoro-3-chlorophenyl)-pyrrole of melting point 149° C. are obtained.

Preparation of the starting compound

EXAMPLE II-1

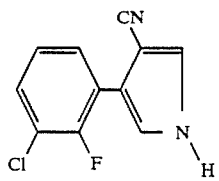

A solution of 6.0 g (0.0331 mole) of 3-(2-fluoro-3-chlorophenyl)-acrylonitrile and 7.8 g (0.0431 mole) of p-toluenesulphonylmethyl isocyanide in 20 ml of a mixture of tetrahydrofuran/dimethyl sulphoxide (5:1) is added dropwise, with stirring and at −10° C. to −20° C. to 1.4 g (0.0464 mole) of sodium hydride (80% strength in mineral oil) in 17.5 ml of tetrahydrofuran under an argon gas protective atmosphere. When the addition is complete, the reaction mixture is allowed to come to room temperature, water is added, the mixture is extracted several times using ethyl acetate, and the combined ethyl acetate phases are washed with water, dried over sodium sulphate and evaporated in vacuo. The residue is purified by chromatography on silica gel (eluent: cyclohexane/ethyl acetate 5:1).

3.3 g (45% of theory) of 3-cyano-4-(2-fluoro-3-chlorophenyl)-pyrrole of melting point 180° C.–181° C. are obtained.

EXAMPLE VIII-1

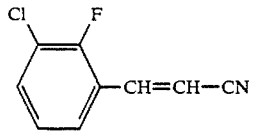

2.5 ml of pyridine and 22.9 g (0.27 mole) of cyanoacetic acid are added to a solution of 40.1 g (0.25 mole) of 2-fluoro-3-chlorobenzaldehyde (cf., for example, DE 3,129,274) in 170 ml of pyridine, and the mixture is heated at reflux temperature for 14 hours. For working up, the mixture is concentrated in vacuo, the residue is taken up in ethyl acetate, the mixture is washed in succession with 1-normal hydrochloric acid, with aqueous sodium hydrogen sulphite solution and with water, dried over sodium sulphate and concentrated in vacuo. The oil which remains can be purified by chromatography on silica gel (eluent: cyclohexane/ethyl acetate 5:1).

16.9 g (37% of theory) of 3-(2-fluoro-3-chlorophenyl)-acrylonitrile of melting point 90° C.–92° C. are obtained.

The following 3-cyano-4-phenyl-pyrrole derivatives of the general formula (I)

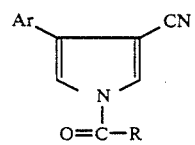

are obtained in a corresponding manner and in accordance with the general preparation instructions:

| Example No. | Ar | R | Melting point [°C.] |
|---|---|---|---|
| 3 | | —CH$_2$—OCH$_3$ | 119–120 |

Use Examples

In the following Use Examples, the compounds listed below were used as comparison substances:

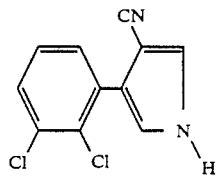

3-Cyano-4-(2,3-dichlorophenyl)-pyrrole
(cf. EP 174,910 and EP 236,272)
and/or

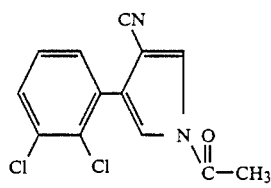

1-Acetyl-3-cyano-4-(2,3-dichlorophenyl)-pyrrole
(cf. DE-OS (German Published Specification) 2,927,480).

EXAMPLE A

Botrytis test (bean)/protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after the inoculation, the site of the infected spots on the leaves is evaluated.

In this test, for example, the compounds of Preparation Examples 1 and 3 show a clearly superior activity compared with the prior art.

EXAMPLE B

Pyrenophora teres test (barley)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dewmoist. After the spray coating has dried on, the plants are sprayed with a conidia suspension of Pyrenophora teres. The plants then remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, for example, the compounds of Preparation Examples 1 and 3 how a clearly superior activity compared with the prior art.

It will be understood that the specification and examples are illustrative but not limitative of the present invention and that other embodiments within the spirit and scope of the invention will suggest themselves to those skilled in the art.

We claim:

1. A 3-cyano-4-phenyl-pyrrole of the formula

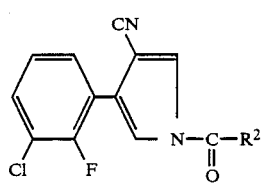

(I)

in which

R$^2$ stands for in each case straight-chain or branched alkyl, alkoxy or alkoxyalkyl, each having 1 to 6 carbon atoms in the individual alkyl moieties.

2. A 3-cyano-4-phenyl-pyrrole according to claim 1, in which

R$^2$ stands for in each case straight-chain or branched alkyl, alkoxy or alkoxyalkyl, each having 1 to 4 carbon atoms in the individual alkyl moieties.

3. A 3-cyano-4-phenyl-pyrrole according to claim 1, in which

R$^2$ stands for methyl, ethyl, methoxy, ethoxy, methoxymethyl or ethoxymethyl.

4. A compound according to claim 1, wherein such compound is 1-acetyl-3-cyano-4-(2-fluoro-3-chlorophenyl)-pyrrole of the formula

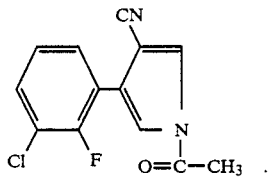

5. A compound according to claim 1, wherein such compound is 1-ethoxycarbonyl-3-cyano-4-(2-fluoro-3-chlorophenyl)-pyrrole of the formula

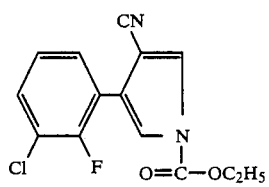

6. A compound according to claim 1, wherein such compound is 1-methoxyacetyl-3-cyano-4-(2-fluoro-3-chlorophenyl)-pyrrole of the formula

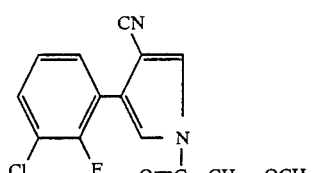

7. A fungicidal composition comprising a fungicidally effective amount of a compound according to claim 1 and a diluent.

8. A method of combating fungi which comprises applying to such fungi or to a fungus habitat a fungicidally effective amount of a compound according to claim 1.

9. The method according to claim 8, wherein such compound is
1-acetyl-3-cyano-4-(2-fluoro-3-chlorophenyl)-pyrrole,
1-ethoxycarbonyl-3-cyano-4-(2-fluoro-3-chlorophenyl)-pyrrole, or
1-methoxyacetyl-3-cyano-4-(2-fluoro-3-chlorophenyl)-pyrrole.

* * * * *